US009428790B2

(12) United States Patent
De Laat et al.

(10) Patent No.: US 9,428,790 B2
(45) Date of Patent: Aug. 30, 2016

(54) SIMULTANEOUS MEASUREMENT OF THROMBIN GENERATION AND CLOT STRENGTH IN PLASMA AND WHOLE BLOOD

(71) Applicant: SYNAPSE B.V., Maastricht (NL)

(72) Inventors: Bas H. De Laat, Maastricht (NL); Hendrik Coenraad Hemker, Maastricht (NL); Leonie Pelkmans, Maastricht (NL); Hilde Kelchtermans, Meeuwen-Gruitrode (BE)

(73) Assignee: SYNAPSE B.V., Maastricht (NL)

( * ) Notice: Subject to any disclaimer, the term of this patent is extended or adjusted under 35 U.S.C. 154(b) by 0 days.

(21) Appl. No.: 14/407,540

(22) PCT Filed: Jun. 20, 2013

(86) PCT No.: PCT/EP2013/062949
§ 371 (c)(1),
(2) Date: Dec. 12, 2014

(87) PCT Pub. No.: WO2013/190071
PCT Pub. Date: Dec. 27, 2013

(65) Prior Publication Data
US 2015/0118691 A1    Apr. 30, 2015

(30) Foreign Application Priority Data

Jun. 21, 2012 (EP) ..................... 12173053

(51) Int. Cl.
| | |
|---|---|
| *C12Q 1/56* | (2006.01) |
| *G01N 11/14* | (2006.01) |
| *G01N 33/49* | (2006.01) |
| *G01N 33/86* | (2006.01) |
| *G01N 33/58* | (2006.01) |

(52) U.S. Cl.
CPC .............. *C12Q 1/56* (2013.01); *G01N 11/14* (2013.01); *G01N 33/4905* (2013.01); *G01N 33/582* (2013.01); *G01N 33/86* (2013.01); *G01N 2333/974* (2013.01)

(58) Field of Classification Search
None
See application file for complete search history.

(56) References Cited

U.S. PATENT DOCUMENTS

| | | | |
|---|---|---|---|
| 5,192,689 A | 3/1993 | Hemker et al. | |
| 6,571,610 B1* | 6/2003 | Raffer | G01N 11/14 73/54.23 |
| 8,916,356 B2* | 12/2014 | Hemker | C12Q 1/56 435/13 |
| 2004/0126874 A1 | 7/2004 | Sakai et al. | |
| 2010/0273206 A1 | 10/2010 | Rauh et al. | |
| 2015/0305681 A1* | 10/2015 | Nadkarni | A61B 5/7246 600/369 |

FOREIGN PATENT DOCUMENTS

| | | |
|---|---|---|
| EP | 0 420 332 A2 | 4/1991 |
| WO | 03/093831 A1 | 11/2003 |
| WO | 2006/117246 A1 | 4/2006 |
| WO | 2008/099179 A2 | 2/2008 |
| WO | WO 2008/099179 * | 8/2008 |
| WO | 2009/098313 A1 | 8/2009 |
| WO | 2011/094185 A1 | 8/2011 |

OTHER PUBLICATIONS

Hemker H. et al. Calibrated Automated Thrombin Generation Measurement in Clotting Plasma. Pathophysiology of Haemostasis and Thrombosis 2003:4-15.*
Van Berkel S. et al. Fluorogenic Peptide Based Substrates for Monitoring Thrombin Activity. ChemMedChem 7(4)606-617, Apr. 2012.*
Hemker H C et al.: "Calibrated Automated Thrombin Generation Measurement in Clotting Plasma", Pathophysiology of Haemostasis and Thrombosis, Karger, CH, vol. 33, No. 1, Jun. 1, 2003, pp. 4-15, XP008053802, ISSN: 1424-8832, 001: 10.1159/000071636 Ap.5, col.2, para.7-p. 6, col. 2, para.3.
Saskia E.M. Schols et al.: "Effects of plasma dilution on tissue factor-induced thrombin generation and thromboelastography: partly compensating role of platelets", A Transfusion vol. 48. No. 11. Nov. 1, 2008. pp. 2384-2394. XP055043790, ISSN: 0041-1132. 001: 10.IIII/j.1537-2995.2008.01872.x abstract; p. 2386. paragraphs "Thrombin generation measurements" and "TEG measurements" Abstract only.
Richey et al.: "Interactions of Associative Thickeners with Paint Components as Studied by the Use of a Fluorescently Labeled Model thickener", XP-000852766, This paper was awarded first prize in the 1990 roon awards competition, vol. 63, No. 798, Jul. 1991.
International Search Report, dated Jan. 30, 2014, from corresponding PCT application.

* cited by examiner

*Primary Examiner* — Ralph Gitomer
(74) *Attorney, Agent, or Firm* — Young & Thompson (57) ABSTRACT

A method for the simultaneous measurement of proteolylic enzyme generation and clot strength in plasma or whole blood or any appropriate biological sample derived from blood. The measurement method encompasses the use of a detectable substrate which includes a moiety that can be released upon reaction with the targeted proteolytic enzyme, and elements for measurement of an increase in viscosity of clot strength.

17 Claims, 8 Drawing Sheets

Figure 1: example thrombin generation WB CAT

Figure 4: Rheometer in oscillation; whole blood

Figure 5a: blood flow simulation in rheometer; plasma

Figure 5b: blood flow simulation in rheometer; whole blood

| Viscosity (mPas) | 100/s | 300/s | 800/s | 1200/s |
|---|---|---|---|---|
| Base level: | 4,03 | 3,25 | 3,03 | 2,92 |
| Plateau level: | 16,55 | 6,00 | 4,51 | 3,97 |
| Lag time: | 1,66 | 1,80 | 1,92 | 1,90 |
| Time to plateau: | 2,60 | 2,89 | 2,81 | 2,64 |

Figure 6: effect of Doolittle peptide

Figure 7: effect of defibrinylation plasma

Figure 8: plasmin generation

SIMULTANEOUS MEASUREMENT OF THROMBIN GENERATION AND CLOT STRENGTH IN PLASMA AND WHOLE BLOOD

The present invention relates to the simultaneous measurement of proteolylic enzyme generation and clot strength in plasma or whole blood or any appropriate biological sample derived from blood. The measurement method encompasses the use of a detectable substrate which comprises a moiety that can be released upon reaction with the targeted proteolytic enzyme, and means for measurement of an increase in viscosity of clot strength.

The invention relates in particular to a method to simultaneously measure the generation of thrombin and the strength of the clot in a blood sample or in biological sample derived from blood. Thrombin generation is detected by a substrate that emits a signal due to cleavage by thrombin. Clot strength is detected on the basis of increased viscosity during clot formation.

In the context of the invention, a special plate-and-cone rheometer was designed which is capable of measuring both thrombin generation and clot strength. The sample holder of the rheometer has a transparent bottom to enable transference of fluorescent light emitted by a thrombin-sensitive substrate. For detection of the thrombin generation, a fluorescent detector advantageously used when the substrate for thrombin comprises a fluorescent moiety and it is placed beneath the sample.

Accordingly the invention relates to the field of hemostasis (or haemostasis) and thrombosis, leading to coagulation in physiological or respectively pathological setting.

The invention accordingly relates to means and methods suitable for investigation of hemostasis and coagulation. Accordingly, the invention provides means, in particular compounds, apparatus, kits and methods for the detection of hemostasis, coagulation or clotting disorders in biological samples comprising blood or blood products such as plasma.

The invention applies in particular to the diagnosis field and accordingly provides means that are suitable to be encompassed in screening tests for detection of a clinical condition of a patient, and especially for the diagnosis of a pathological condition in a patient, such as thrombosis or bleeding risk. The invention also provides means that can be encompassed within screening tests aiming at providing relevant data for therapy planning.

The invention further relates to therapy monitoring of a patient, especially when said patient is under drug treatment.

The invention may also be used for the determination of the activity of pharmaceutical agents or drugs on the process of coagulation and fibrin clot formation, or for the assessment of activity of drug candidates in such process.

Hemostasis is a balance between prothrombotic and bleeding state. Components of hemostasis can be divided into a plasma part which is a solution derived from blood containing the coagulation proteins, and a cellular part of blood containing blood cells such as platelets, erythrocytes and leucocytes. In vivo interaction of the vessel with the hemostatic system prevents excessive blood loss when damage to a vessel occurs. One of the central coagulation proteins in the hemostatic system is thrombin. Thrombin is formed at the end of the coagulation cascade and causes fibrinogen to be converted into fibrin. The formed fibrin forms a tight mesh capturing platelets and erythrocytes thus giving rise to a plug that seals off the vessel. The measurement of thrombin generation is known to be indicative for either a prothrombotic or a bleeding phenotype and the formation of fibrin has been shown to be indicative of a bleeding phenotype related to point of care devices during surgery. Blood clot firmness is an important functional parameter for haemostasis in vivo, as a clot must resist blood pressure and shear stress at the site of the injury.

The medical world has been able to measure changes in the hemostatic system related to pathophysiology for decades. In the early 50ies it was discovered that thrombin has a central role in hemostasis and that measuring the generation of thrombin gives a good indication of the status of the coagulation system overall. The group of prof. Hemker (NL) has put much effort into designing an assay to measure thrombin generation in time in the presence of a calibrator. They succeeded to design and manufacture a method used as such in whole blood, plasma and platelet rich plasma which is known as Calibrated Automated Thrombography (WO 03/093831). Nowadays this method is used in many research laboratories. Several methods can be used to measure thrombin generation in plasma and whole blood. Hemker et al. showed the principle of a thin layer diminishing the effect of erythrocytes in combination with a rhodamine-based substrate insensitive for erythrocyte quenching (WO 2006/117246). The combination proved to be a powerful tool for measuring thrombin generation in whole blood.

At this moment all methods to measure thrombin generation are based on the single detection of thrombin, mostly by conversion of a thrombin-sensitive fluorescent/chromogenic substrate. Thrombin is the key enzyme converting fibrinogen into fibrin. In addition, a relation has been shown between the rate of thrombin conversion and the fibrin thickness and branching. Despite the importance of thrombin and its association with bleeding or prothrombotic phenotype there are several conditions in which fibrin, and thereby clot strength, can be influenced independently from thrombin. The group of Konings et al. showed that coagulation factor XIIa strengthens the fibrin network independently of thrombin [1]. Therefore there is a need for simultaneous measurements of thrombin generation and the strength of a clot. Additionally, by the simultaneous measurement of thrombin generation and clot strength, the minimal amount of thrombin necessary for clot initiation can be determined readily.

The present invention provides methods, devices and kits that enable fulfilling this need, which means may further be adapted to simultaneous measurement of various proteolytic enzymes activity involved in hemostasis or thrombosis together with the strength of clot.

Principles of Hemostasis and Coagulation Related to the Invention

Mechanism of Thrombin Generation

The mechanism of thrombin generation in blood plasma can be exemplified as follows. Tissue factor (TF) is abundantly-but not exclusively- present in the vessel wall. When a blood vessel is damaged, the blood enters the tissues and the plasma protein factor VIIa (VIIa) can interact with TF. This triggers a complex set of interactions between plasma proteins and blood platelets, resulting in a transient burst of thrombin that remains limited in time and space. Therefore, a wound stops bleeding but clotting is not propagated to the remainder of the body.

This mechanism can be shown to be so intricate, replete with positive and negative feedback reactions, that its action cannot be predicted from knowledge of its parts (irreducible complexity). Therefore, if one wants to assess the function of the haemostatic system, the thrombin generation has to be investigated as it occurs in the body or in an isolated part of the body, i.e. a sample of blood or platelet-rich plasma. The interaction between blood platelets and plasma factor is of particular importance, the information to be obtained from platelet-poor plasma being essentially deficient [3-5].

An important fraction (approximately 30%) of all thrombin formed in clotting plasma is bound to the fibrin clot. Clot-bound thrombin does retain its thrombotic properties, it can clot fibrinogen, activate factors V, VIII and XI as well as platelets [3-5]. It is however only partly inhibited by antithrombin. Therefore, it is essential that fibrin is present when investigating the function of the coagulation system.

As stated before, the thrombin activity that generates at the site of a lesion is an important determinant of the extent of the haemostatic-thrombotic reaction that ensues. Most of the thrombin (>95%) is generated after the moment of clotting, therefore the clotting time is not automatically a good indicator of thrombin activity. Thrombin activity in clotting blood is a transient phenomenon and therefore should be measured during the clotting process.

Figure 1:
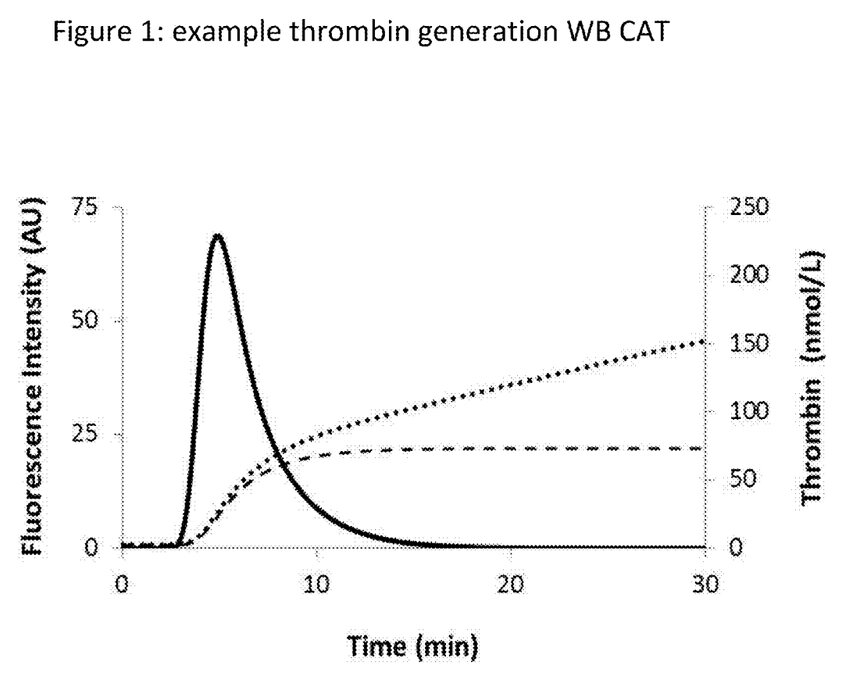
FIG. 1 shows a typical thrombin generation curve in whole blood generated by the whole blood CAT-based assay.

A typical course of thrombin formation in clotting blood or plasma, also designated as the thrombin generation curve, is shown in FIG. 1 (solid line). After a period in which no observable thrombin is formed, the concentration steeply goes up, rises to a peak and then goes down again. The typical parameters of the thrombin formation are the lag time, the area under the curve (AUC), also designated as the endogenous thrombin potential (ETP; see below), the peak height, and the time it takes to reach the peak.

Clot Strength

The formation of fibrin clots that are relatively resistant to lysis represents the final step in blood coagulation, leading to repair of the tissue injury. The complex process of clot formation is initiated by the cleavage of N-terminal peptides, known as fibrinopeptides A and B, from fibrinogen. These activated fibrinogen molecules can form soluble complexes with fibrin and fibrinogen molecules (fibrin monomers). In case of persistent thrombin activity, the concentration of soluble fibrin increases and forms long, double-stranded protofibrils. Subsequently, these protofibrils can be combined laterally to form fibrin fibers of varying diameters, resulting in polymerization of soluble fibrin into covalently bonded polymerized insoluble fibrin.

The structure of the fibrin clot can be influenced by a number of variables, including the local pH, ionic strengths, and concentrations of calcium and fibrinogen. Importantly, the concentration of thrombin present at the site has the most profound physiologic effect on fibrin clot structure. Low thrombin concentrations produce very turbid, highly permeable fibrin clots composed of thick, loosely-woven fibrin strands. Higher thrombin concentrations produce relatively non-turbid, less permeable clots composed of a dense network of relatively thin fibrin strands. By thrombin-dependent activation of factor XIII, covalent bonds between different fibrin chains are formed, reinforcing fibrin contacts within the fibrin clot and thereby increasing the viscoelastic properties of the fibrin clot. The fibrin structure strongly determines the mechanical and fibrinolytic stability of the clot, and may have significant physiologic implications. Firm clots that are resistant to fibrinolysis are prone to thrombosis while fragile clots, highly susceptible to fibrinolysis, result in premature lysis and bleeding.

Most studies of clot formation have been performed by adding a fixed amount of purified thrombin to fibrinogen. However, in vivo, clot formation occurs in the presence of continuous, dynamic concentrations of thrombin. These complex kinetics lead to relatively heterogeneous fibrin architecture in clots formed during in situ thrombin generation, versus the homogeneous fiber architecture present in clots produced by the addition of exogenous thrombin. Additionally, possible involvement of further components of the coagulation system such as FXIIa, independently of thrombin generation may impact the fibrin clot structure. Taken together, there is a need for simultaneous measurements of thrombin generation and fibrin formation/clot strength.

Methods of the Prior Art

Determination of Thrombin Generation in the Prior Art

A thrombin generation curve was classically obtained via determination of the thrombin content in small subsamples taken at short intervals from clotting blood or plasma[6, 7]. This method generally requires separate analysis of the subsamples and allows the determination of only 3-5 curves simultaneously by the continuous occupation of a skilled laboratory worker. It is so labor intensive as to preclude its application in clinical or pharmaceutical routine.

EP-A-0 420 332 (or U.S. Pat. No. 5,192,689) discloses a method to determine the amount of thrombin which has been present in a sample of either clotting blood or plasma by measuring the amount of product that is produced from an artificial substrate during coagulation. This amount is proportional to the area under the thrombin generation curve, designated as the Endogenous Thrombin Potential, ETP. The method comprises adding a thrombin formation activator to a sample of either clotting blood or plasma together with a thrombin substrate, wherein the amount and also the kinetic properties of the thrombin substrate are chosen such that the amount of thrombin generated in the sample cannot completely consume said thrombin substrate, thereby producing a conversion product, measuring the amount of said conversion product thus produced and, from this, determining the endogenous thrombin potential in the sample. This ETP-method can be illustrated by the following reactions:

1) Clotting factors (V-XII)→prothrombinase by activator
2) Prothrombin→thrombin by prothrombinase
3) Thrombin+antithrombotics→inactive complexes
4) Substrate→signal molecule by thrombin All reactions are irreversible and therefore thrombin is only temporarily present in the reaction mixture. While thrombin is present, it participates in reaction 4, with the result that the degree of conversion of the substrate indicates the time for which, and the time to which, thrombin has catalyzed this reaction.

It is essential that the amount of substrate should not be exhausted before the thrombin disappears. For the amount of substrate converted to be an exact representation of the total amount of thrombin activity that developed, the reaction rate should be proportional to the concentration of thrombin at any instant in time. The essence of this ETP method is that the thrombin potential is determined as an end-point method without determination of the thrombin/time curve as such. In case the substrate would be short-measured, the end-point would be simply the maximum amount of product formed, and such figure has no meaning anyway.

Furthermore, the ETP-method is conducted in actual practice with a chromogenic substrate i.e. substrates with a chromophoric leaving group that is detected via optical density measurement. Fibrinogen, and consequently blood platelets, have to be removed from plasma because turbidity arising from the fibrinogen-fibrin conversion by thrombin makes further measurement impossible. Fibrinogen and platelets, however, are essential components of the clotting system that influence the course of thrombin formation. This puts a serious limit on the applicability of optical density as a detection method. Thus, assessment of the ETP in plasma containing platelets and/or fibrinogen would not be possible.

Continuous monitoring of thrombin concentration has been attempted through adding a suitable thrombin substrate to the clotting sample and monitoring the time course of appearance of the amidolytic split product. For example, a chromogenic substrate is used and the optical density is measured so as to monitor the development of p-nitro-aniline [8, 9]. If the reaction velocity in such a test would be dependent upon thrombin concentration only and if the signal would be proportional to the amount of product, then the slope of the product curve would be proportional to the amount of thrombin present, so that the thrombin generation curve can be obtained from the first derivative of the product curve if the proportionality constant (Kc) is known.

In practice, however, the reaction velocity is not dependent upon the thrombin concentration only, the signal is not necessarily proportional to the amount of product and Kc is unknown. The reasons are the following:

A: Substrate consumption: The signal is not only dependent upon the activity of thrombin in the sample but also on the amount of substrate which, through the very enzyme activity itself, decreases in time. The effect can be attenuated by adding an excess of substrate but to a certain limit only. The substrate binds, reversibly, to the active centre of thrombin and thereby protects thrombin from inactivation by natural antithrombins. Abolishing the effect of substrate consumption to an acceptable degree is paid for by prolonging the experiment to last for about two hours. (The more substrate is added the more enzyme molecules are occupied and unavailable to the natural inactivation processes. This prolongs the duration of the experiment. At 1×Km the experiment is finished in 30 min, at 5 Km practical independence of substrate consumption is obtained but the experiment lasts 90 min). Also, at such concentrations of substrate, thrombin inhibition interferes with feedback reactions and it is no longer guaranteed that the natural process is measured. This is also the reason why, in a method meant to assess the area under the curve from the total amount of substrate converted, an excess of substrate has to be added such that extra antithrombin needs to be added in order to make the experiment practically possible (see EP-A-0 420 332, discussed above). B: Changes in optical density occur through clotting of the plasma sample: the use of chromogenic substrates implies the removal of fibrinogen, and consequently blood platelets, that causes spurious increase of OD through scattering of light at the moment of clotting. Fibrinogen and platelets, however, are essential components of the clotting system that influence the course of thrombin formation (see above). This puts a serious limit on the applicability of optical density as a detection method. This problem can be circumvented by using a substrate that yields a fluorescent product [10]. This, however, introduces the next problem: C: In fluorescence measurements the signal is not linearly related to the amount of product. Notably the fluorescent signal is not linearly dependent upon the concentration of fluorescent product because fluorescent molecules absorb the light from other product molecules, the so called "inner filter effect". With fluorescent products, increasing substrate concentrations to several times Km, as required for limiting the effect of substrate consumption automatically also increases the inner filter effect.

Problem A is common to all continuous methods. Problem B can be circumvented by using a fluorogenic substrate but this introduces problem C. D: Even if the problems A, B and C would not exist, the question remains of establishing a relevant relationship between reaction velocity to thrombin concentration, i.e. determining the calibration constant Kc. This relation varies from experimental setup to experimental setup (e.g. is different in different fluorometers) and from sample to sample (e.g. due to color variations of the plasma). Addition of a known standard amount of thrombin to the sample is impossible because the enzyme added will disturb the physiological reactions. It is also impossible to add thrombin to a parallel non-clotting sample because it will be inactivated in the plasma.

These drawbacks were conveniently obviated by measuring the concentration of thrombin in clotting plasma, with or without platelets, by monitoring the splitting of a suitable signal substrate and comparing it to a constant known thrombin activity in a parallel sample, as described in patent application WO 03/093831. The method is based upon the finding that certain substances exhibit a constant thrombin-like activity which can be suitably used to assign absolute values (nM) to the first derivatives of the signals obtained from molecules that are split by thrombin as it develops in and disappears from clotting plasma. A suitable and particularly preferred calibrator is the irreversible complex of $\alpha_2$-macroglobulin (also designated herein as $\alpha_2 M$) and thrombin. Binding of thrombin to $\alpha_2 M$ renders thrombin immune to the natural inactivators present in plasma but leaves intact its capacity to split small substrates that upon cleavage release a molecule with light absorptive-, fluorescent-, or other signal-bearing properties.

More particularly, in one part of the sample, thrombin generation (i.e. coagulation) is triggered by a method known in the art. To the other part a preparation with independently determined and invariable thrombin activity, preferably the $\alpha_2 M$-thrombin complex, as mentioned above, is added. Product formation is measured in the two samples preferably at the same time. The exact molar amount of thrombin present at any moment in the coagulating sample is obtained by comparison of the signal from that sample to the measured signal from the sample to which the preparation with known and invariable thrombin activity has been added but in which thrombin formation has not been triggered. Resulting curves produced by this method are characterised by parameters as lag time, area under the curve, peak height, steepness of ascending slope, time to peak and further all parameters of a curve that resembles the mathematical function $T=a.t\ b.\exp\text{-}ct$ (starting after a lag time). The concentration of thrombin typically starts at zero, rises to a peak height of usually a value between 50 and 500 nanomolar and goes back to zero again. The lag time is usually a value between zero and 20 minutes and is finished as soon as the thrombin concentration is approximately above 10 nanomolar. At this moment also the formation of a clot appears, whereas the peak occurs a few minutes later. The parameters of the thrombin generation curve, also designated as Thrombogram®, a registered trademark of Synapse B.V., are composite parameters that are influenced by a large set of concentrations and reaction constants of the interacting clotting factors. They reflect all variations of these variables that influence the function of the haemostatic thrombotic system such as they take place in a clinical, therapeutical or other setting. All antithrombotics and all diseases related to the haemostatic thrombotic system measured thus far have their influence on these parameters. During antithrombotic treatment or haemostatic coagulation disorders of any kind lag times and time to peak values are usually increased, peak height and area under the curve are usually decreased. On the other hand under hypercoagulable states these parameters move into the opposite direction. In this way the Thrombogram truly reflects the clottability of blood and gives an indication for either thrombotic or haemostatic risk.

Using this calibrated automated thrombogram (CAT) assay developed by Hemker and co-workers, thrombin generation in plasma is most accurately measured. However, variable quenching of the fluorescent signal by hemoglobin and red blood cells that sediment, cluster and retract with the clot, may lead to highly erratic signals. Subsequently, it has been demonstrated (WO 2006/117246 and WO 2009/098313) that the problems caused by red blood cells can be overcome by dispersing the blood in the sample holder thereby creating a thin layer of blood. Using rhodamine-110 as a signaling product, a fluorogenic substrate with high quantum yield, excitation and emission wavelengths that have less overlap with the absorption spectrum of hemoglobin and that is not significantly consumed over time (submitted for publication) has also improved the system.

FIG. 1 shows the conversion of the raw fluorescence data (dotted line) to the thrombin activity for the whole blood CAT. The increase in fluorescence intensity due to formation of $\alpha2M$-thrombin activity was substracted from the total fluorescence intensity (dashed line). The first derivative of this corrected fluorescence-time curve and conversion of fluorescence intensity with the calibrator yields a thrombogram with the thrombin activity expressed as nM (solid line). From this thrombogram, the following parameters can be calculated: endogenous thrombin potential (ETP, area under the curve; nM.min), lag time (min), thrombin peak (nM) and time-to-thrombin peak (min).

Patent application WO2011/094185 refers to the basic method described above in EP-A-0 420 332 and discloses a method for measuring generation of thrombin in a sample of blood as a function of time using an improved fluorometer. A fluorogenic substrate and a thrombin activator are added to the sample of blood to form an activated sample. Fluorescence is measured with the use of a fluorometer and thrombin generation as a function of time is calculated from the measured fluorescence.

Document WO 2008/099179 discloses a method to measure rheological properties of clotting blood, using an oscillating rheometer comprising a base surface and an oscillating surface containing a gap for the introduction of a blood sample. Major drawbacks of the oscillation mode compared to the rotary mode are: (1) extreme low shear rates in oscillation mode which are more comparable to static measurement; (2) duration of the test is 2-3 times longer than in rotational mode; in rotational mode the test occurs mostly in laminar flow as in the human body.

Document U.S. Pat. No. 6,571,610 discloses a rotary rheometer having a base element in the form of a plate and a rotary element in the form of a cone. A gap for the introduction of a sample to be tested is formed between the base element and the rotary element.

An important feature of the cone and plate geometry is the homogenous shear rate or linear velocity profile throughout the gap enabling homogeneous flow characteristics in the middle and the edges of the sample.

Determination of Strength of a Clot in the Prior Art

Fibrin formation can be monitored by the detection of the increase in viscosity. In this 'viscosity detection' method, a magnetic element is placed in the plasma. Due to the initiation of the coagulation reaction, that is fibrin formation, the motion of the magnetic element becomes slower and the velocity of this motion can be detected. Disadvantages of this system include the production of variable results depending on the shape of the formed fibrin clumps. Additionally, coagulation can only be measured when the viscosity reaches a specific level. For example, routine hemostasis analysers determine clot formation by measuring variations of a magnetic ball oscillation amplitude through inductive sensors. The movement of the ball is obtained by an alternate electromagnetic field created by two independent coils. The oscillation amplitude remains constant as long as the viscosity of the surrounding fluid is constant, but decreases when the environment viscosity increases. The position of the ball in the cuvette determines the signal received by the receiver coil. These magnetic field variations determine the oscillation amplitude and the clotting time.

Another technique, thromboelastography (TEG), mechanically investigates clot formation (or dissolution) in an oscillating system [11]. In the conventional TEG, a cup is in oscillation motion around a measuring pin, while in ROTEM (rotation thromboelastometry) the cup is fixed and the pin brought into oscillation rotational motion. Upon initiation of clot formation, fibrin strands are formed, resulting in an increased torque between the pin and cup. This change in torque can be detected electronically (TEG) or optically (ROTEM). The visco-elastic change after induction of coagulation stems partly from the fibrin meshwork which is formed and partly from the aggregation of activated platelets, von Willebrand Factor (VWF) and fibrin. Therefore, it is sensitive to platelet and fibrinogen levels in whole blood coagulation. Importantly, in contrast to many of the conventional coagulation tests that end with the formation of the first fibrin strands, TEG continues generating data up to eventual clot lysis/retraction. TEG thereby provides information about fibrinolytic activity and platelet function, which is not generally available from routine coagulation tests. For example, determination of the change in viscoelasticity can be used to assess quantitative/qualitative deficiencies of von Willebrand Factor and platelet function defects resulting in reduced interaction of VWF with platelets, as outlined in US 2010/0273206 A1. A possible disadvantage of TEG is that it is performed under low shear conditions (0.1 per second), resulting in the entrapment of the red cell mass in the fibrin network, possibly interfering with the spreading of the fibrin strands or with the interaction of fibrin with platelets. Therefore, TEG should be interpreted along with hematocrit values of the blood sample. As other in vitro methods, it cannot reflect the in vivo contribution of endothelial cells or shear forces of blood flow on local clot formation and fibrinolysis [11]. Using fibrin as an indicator for thrombin generation in whole blood, as in TEG, does not reflect the total thrombin generating capacity in patients, given the fact that fibrinogen as a substrate is quickly exhausted and therefore fibrin measured in TEG only informs about thrombin generation at an early phase of the coagulation process. Mathematical treatment of the TEG signal aiming to resemble a thrombin generation curve does not contribute except to confusion [12, 13].

SUMMARY OF THE INVENTION

The present invention aims at providing a method that overcomes the drawbacks of the prior art at least in part and which relies on the simultaneous measurement of both thrombin generation and fibrin formation/clot strength, in a biological sample assayed in vitro. The present invention provides furthermore a method which can be applied to measurement of generation of other proteolytic enzymes active in haemostasis or thrombosis, such as plasmin, thus enabling simultaneous measurement of both proteolytic enzyme activity and fibrin formation/clot strength.

Such a method provides in particular a measurement system reflecting enzymatic activity, in particular thrombin activity, that occurs in vivo.

Despite the strong relation between the rate of thrombin conversion and fibrin thickness, there are several conditions in which fibrin can be influenced independently from thrombin, supporting the need for simultaneous detection of thrombin generation and fibrin formation. The present invention relates to a method enabling the simultaneous measurement of a proteolytic activity, in particular thrombin generation, and clot strength in real time.

The present invention relates to the simultaneous measurement of thrombin generation and the strength of a clot. Thrombin generation may be measured by a method, preferably the CAT-method as described by Hemker et al. [2] and illustrated in the following pages and examples. Clot strength is measured by detecting increased/decreased viscosity using a specially designed rheometer.

Thrombin generation is preferably measured by detection of the fluorescent light emitted by a thrombin-sensitive substrate. As to detection of the clot strength, the biological sample (either blood or plasma) is applied on a rheometer which is designed to be sensitive enough to detect an increase in viscosity due to the formation of fibrin. Importantly, the use of this specially designed rheometer enables the application of different shear rates to the coagulation reaction. Thereby, this invention describes a method to in vitro study thrombin generation and clot strength in conditions resembling shear rates in in vivo venous and arterial blood flow, providing relevant information on platelet function and fibrinolysis. The simultaneous measurement of thrombin generation and clot strength has the additional advantage to readily determine the minimal amount of thrombin necessary for clot initiation.

The invention also relates to a rotary rheometer for measuring properties, in particular clot strength, of a biological sample, comprising a base element and a rotary element defining between them a measuring gap for the introduction of a sample to be tested, means for measuring the rotational speed of the rotary element and/or the torque applied to the rotary element, wherein said rheometer comprises a fluorometer for quantifying the fluorescence signal emitted by the biological sample.

In a particular embodiment of the rheometer, the rotary element comprises a cone and the base element comprises a plate, the measuring gap being formed between the tip of said cone and said plate. A suitable measuring gap to carry out the method of the invention is for example between 10 µm and 2 mm, preferably not more than 100 µm, determined between the rheometer measuring system (for example between the tip of the cone of the rheometer) and the upper plate of the base part of the rheometer, or the bottom surface of a holder of the sample.

Preferably, the base element and the sample holder comprise a transparent surface enabling the detection and quantification of the fluorescence signal emitted by the sample through said surface by the fluorometer.

DETAILED DESCRIPTION OF THE INVENTION

In the following a typical description of the haemostatic and thrombotic system is given for the present invention with an emphasis on its most important enzyme, thrombin. It is to be noted, however, that the present invention also relates to other enzymes and to other physiological systems, such as other activated proteolytic enzymes (factors) of the clotting system in blood and plasma including, plasmin and other activated components of the fibrinolytic system in blood and plasma, and activated complement factors in blood and plasma.

To simultaneously measure proteolytic enzyme generation, in particular thrombin generation, and clot strength, the assayed biological sample is applied on a rheometer designed to enable detection of an increase of viscosity due to the formation of fibrin in various shear stress conditions mimicking in vivo physiological conditions. The air-beared rheometer is sensitive enough to detect an increase in viscosity due to the formation of fibrin. The transparent bottom of the sample holder enables transference of fluorescent light emitted by a thrombin sensitive substrate, readily detectable with a built-in fluorometer.

The method of the invention, for in vitro simultaneous determination in real time of the course of determined proteolytic enzyme activity and of the strength of the formed fibrin clot in a biological sample, while simulating in vivo blood flow conditions, comprises the following steps:
  a) triggering proteolytic enzyme generation in the biological sample so as to enable clotting in said biological sample and contacting said biological sample with a signal substrate causing a detectable signal related to the conversion product released upon reaction of said signal substrate with the proteolytic enzyme generated,
  b) displaying the sample mixture obtained in a) as a thin layer and setting a measuring gap, in particular a zero gap, between the measuring system and the mixture obtained in a) hold in a vessel suitable for measurement of the detectable signal obtained after reaction of the signal substrate with the proteolytic enzyme,
  c) applying a rotational force to the sample mixture obtained in b), thereby simulating venous or arterial blood flow of a determined in vivo physiological or clinical condition,
  d) determining the time course of detectable signal development in the biological sample to provide results of proteolytic enzyme activity over time, especially as a curve,
  e) on said triggered biological sample, simultaneously monitoring the increase in viscosity over time with a rotary rheometer, as a measure of the formation of fibrin in the biological sample.

The terms "proteolytic enzyme generation" and in particular the terms "Thrombin generation" reflect the appearance and disappearance of the proteolytic enzyme activity, in particular thrombin activity, over time in the triggered biological sample. Accordingly the terms "proteolytic enzyme generation" and "proteolytic enzyme activity" are used interchangeably.

The term "real time" as used herein is meant to indicate that the course of proteolytic enzyme concentration in the medium is displayed simultaneously with the biological activation and inactivation of the sample that is going on in the reaction vessel.

As used herein, the term "signal substrate" means a substrate that is cleaved by a proteolytic enzyme generated in the assayed biological sample present in the medium, from which a leaving group is split off which is detectable. In a particular embodiment of the invention, the signal substrate is a fluorogenic substrate, the leaving group of which is detectable by fluorescence detection,. In particular, the "signal substrate" is a substrate that is cleaved by thrombin. Suitable fluorogenic signal substrates for thrombin are well known for the skilled person and disclosed especially in EP 0420332 or in WO 03/093831.

The expression "thin layer" means a layer of assayed sample having a thickness within a range of 0.05 to 5 mm and in particular within a range of 1 to 3 mm, for example 2 mm or less.

According to the invention, measurement of viscosity as a determination of fibrin formation in the biological sample and determination of proteolytic enzyme generation in said sample are said to be simultaneous because they are performed on a single sample or subsample, e.g., in one single sample vessel or holder.

Advantageously, in a particular embodiment of the invention, the measurement of fibrin formation and determination of proteolytic enzyme generation are carried out using a single apparatus, such as a rheometer, in particular a rotary rheometer according to the invention that is specifically designed to also comprise a fluorometer.

The assayed sample is a biological sample usually consisting of blood i.e., whole blood, or a product derived from blood such as plasma in particular platelet-rich plasma (PRP), platelet-poor plasma (PPP) or platelet-free plasma (PFP). Blood is usually collected in tubes that contain either sodium citrate or EDTA, or the like, so that free calcium ions in the blood are bound and proteolytic enzyme formation, in particular plasmin or thrombin formation and clotting is prevented during sample collection and storage.

The invention provides the possibility of using biological samples, especially blood samples in a range as small as 20 to 60 µl and up to approximately 1 ml.

According to the invention triggering proteolytic enzyme generation is carried out in a known manner, with activation factors. Activation factors, also designated protease activators for carrying out the present method include phospholipids, Tissue Factor, in particular soluble Tissue factor, or recombinant human Tissue Factor, thromboplastin, kaolin, and elagic acid. Depending on the biological sample used, they may be added in the first subsample to trigger proteolytic enzyme activity. They are also advantageously added to the mixture eliciting a constant known proteolytic enzyme activity in particular plasmin or thrombin activity. The activation factors may be used with further components necessary or advantageous to start the coagulation reactions such as calcium ions.

Indeed, in order to start reactions eliciting proteolytic enzyme generation, in particular plasmin or thrombin generation, calcium should be added shortly before the start of the measurement. In an embodiment of the invention, as illustrated in the examples calcium is added as FluCa, i.e., as a mixture of fluorogenic substrate and CaCl2. This FluCa mixture may be prepared as disclosed in the examples. However, in case blood is not collected in sodium citrate, or the like, this addition of calcium may not be necessary and the fluorogenic substrate is thus added as a solution. This may be the case when the method is used in a way that makes it possible to start the experiment within minutes after blood taking.

In a particular embodiment of the invention, the method provides in vitro simultaneous determination in real time of the course of thrombin activity and of the strength of the formed fibrin clot.

When the proteolytic enzyme is thrombin, thrombin activity against time may be presented as a curve of Thrombogram™ (TG) which is characterized by an initiation phase providing minute amounts of thrombin followed by a burst of activity. Blood forms a clot at the very beginning of the burst and almost all thrombin is formed after the clot has formed. The Thrombogram™ thus shows various phases including lag time, propagation phase, time to peak and peak height and ETP.

The term "lag time" as used herein is meant to indicate the time (min) it takes before thrombin formation starts.

As used herein, the term "peak height" (nM) means the maximal thrombin activity attained during the assay on a tested sample.

The term "time to peak" (min), as used herein, means the time between the start of the reaction and the moment that the peak is reached.

The term "ETP" (Endogenous Thrombin Potential), as used herein, means the time integral of the curve until the moment of (near)zero thrombin activity is attained, corresponding to the area under the curve (nM. min).

The signal substrate which is used in the present method is preferably selected from the group of compounds comprising a leaving group, said leaving group providing a detectable conversion product upon reaction of said compound with the proteolytic enzyme formed. This conversion product is determined by spectroscopy. In a particular embodiment the signal substrate is a fluorogenic substrate, and its leaving group emits fluorescence. Accordingly, in a particular embodiment of the invention, said leaving group is a fluorescent group. In a particular embodiment of the invention for thrombin activity measurement, the leaving group, especially the fluorescent group is present on a substrate which is sensible to thrombin and undergoes a splitting reaction of the leaving group.

In a particular embodiment, the signal substrate is a fluorogenic substrate selectively hydrolyzed by thrombin, having a moderate binding affinity for thrombin and a low kinetic constant and in particular is a synthetic substrate for thrombin, coupled with a fluorescent molecule.

In a particular embodiment of the invention, the fluorogenic substrate is an oligopeptide having a sequence of 2 to 30 amino acids residues coupled with a fluorescent molecule. As an example, the oligopeptide has a terminal lysine or arginine for coupling with a fluorescent molecule.

A suitable and preferred signal substrate for carrying out the method of the present invention using a fluorescence detector, on whole blood or plasma is (Z-Gly-Gly-Arg)$_2$Rho110, a rhodamine-based thrombin substrate. Rhodamine is extremely useful given its high quantum yield, excitation and emission wavelengths that have less overlap with the absorption spectrum of hemoglobin, and since it is not significantly consumed during the time of the assay.

Alternatively, for plasma measurements Z-Gly-Gly-Arg-AMC (Backen Switzerland) can be used as a thrombin substrate, which releases AMC (7-amino-4-methylcoumarin) and is measured by a 390 nm excitation and a 460 nm emission filter set.

When the proteolytic enzyme generation measured is the generation of plasmin, the substrate may be bis-(CBZ-L-phenylalanyl-L-arginine amide), dihydrochloride coupled to rhodamine 110. Another fluorogenic substrate suitable for the detection of plasmin generation is H-Ala-Leu-Lys-AMC (Stago, France).

It has been reported in the prior art that in the particular case of measurement of thrombin generation, thrombin and its substrate do not react linearly with each other. In order to compensate for non-linearity of the reaction rate of thrombin with its substrate, depending upon thrombin concentration in the biological sample, measurement of a mixture eliciting a constant known thrombin activity is performed in parallel on a non clotting second part of the assayed sample (second subsample). This step provides calibration for proteolytic enzyme activity measurement in the first part of the sample. Calibration is thus advantageously performed when the measured proteolytic enzyme activity is thrombin activity. Rather plasmin generation measurement can be performed without a calibration step.

Accordingly, in a particular embodiment, for the purpose of carrying out the invention described herein, including a calibration of the proteolytic enzyme activity, the method comprises:

an initial step of dividing the biological sample in at least two parts, designated subsamples, including a first subsample and a second subsample, performing steps a) to e) of the method for the simultaneous detection of determined proteolytic enzyme generation and fibrin formation of the invention are performed on the first subsample and, performing the following steps on the second subsample for calibration of the results of measurement of proteolytic enzyme activity:

f) adding to the non-clotting second subsample, a calibrator compound harbouring a constant stable activity on the signal substrate for said determined proteolytic enzyme said calibrator compound being otherwise inert in the coagulation reactions of the subsample (being inert to physiological antithrombin agents in blood), and contacting the obtained mixture of said calibrator compound and second subsample with a signal substrate causing a detectable signal related to the conversion product released upon reaction of said signal substrate with the proteolytic enzyme of said second subsample, g) submitting said mixture obtained in step f) with the second subsample to steps b) and c) of the method of the invention as defined herein, h) determining the time course of detectable signal development in the second subsample to provide results of proteolytic enzyme activity over time especially as a curve;

i) comparing the results obtained in step g) to the results of proteolytic enzyme activity obtained in step d) to derive calibrated results of proteolytic enzyme activity in time in the first subsample, in particular as a calibrated curve.

Suitable calibrator compound with a constant known stable proteolytic activity for carrying out the method of the present invention, as defined above, include $\alpha_2$M-thrombin complex ($\alpha$2-M-T), staphylocoagulase-prothrombin complex, and gamma thrombin. Alternatively, any proteolytic enzyme can be used which is modified in its secondary recognition sites in that its active center for proteolysis remains intact but its functional interaction with proteins in the reaction mixture is abolished, so that it is regarded as inert in the coagulation reactions taking place in the reaction mixture.

The methods and reagents of the invention are suitable for use in measuring properties of blood to form fibrin clot and properties of blood with respect to proteolytic enzyme generation.

Figure 2:
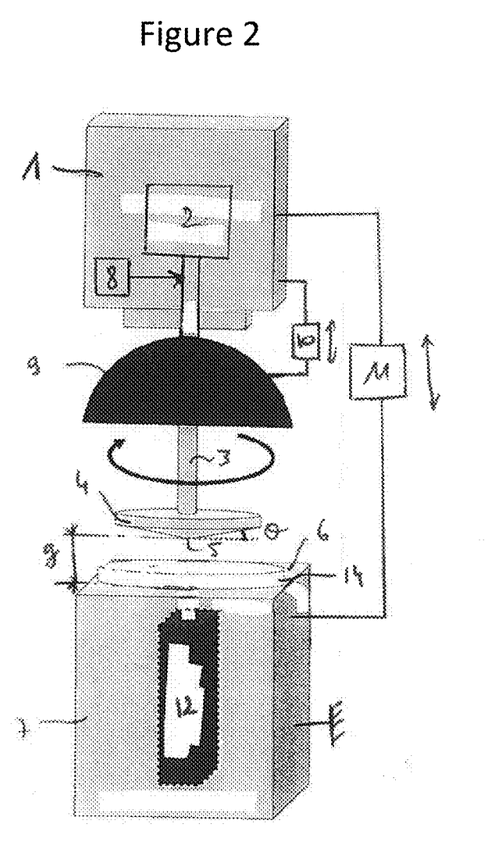
FIG. 2 illustrates a schematic view of a rheometer according to the invention, enabling simultaneous measurement of thrombin generation and clot strength.
Figure 3:
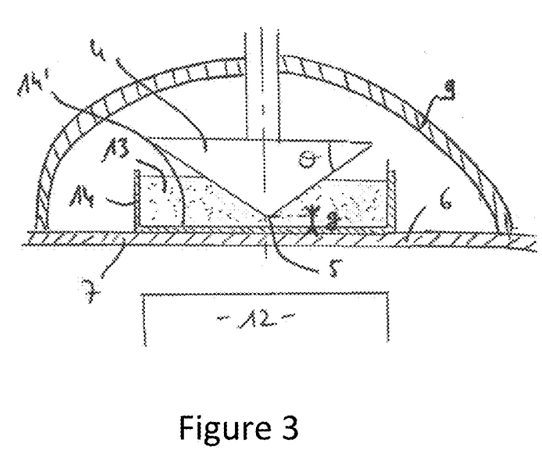
FIG. 3 illustrates a cross-section view of a part of said rheometer.
Figure 4:
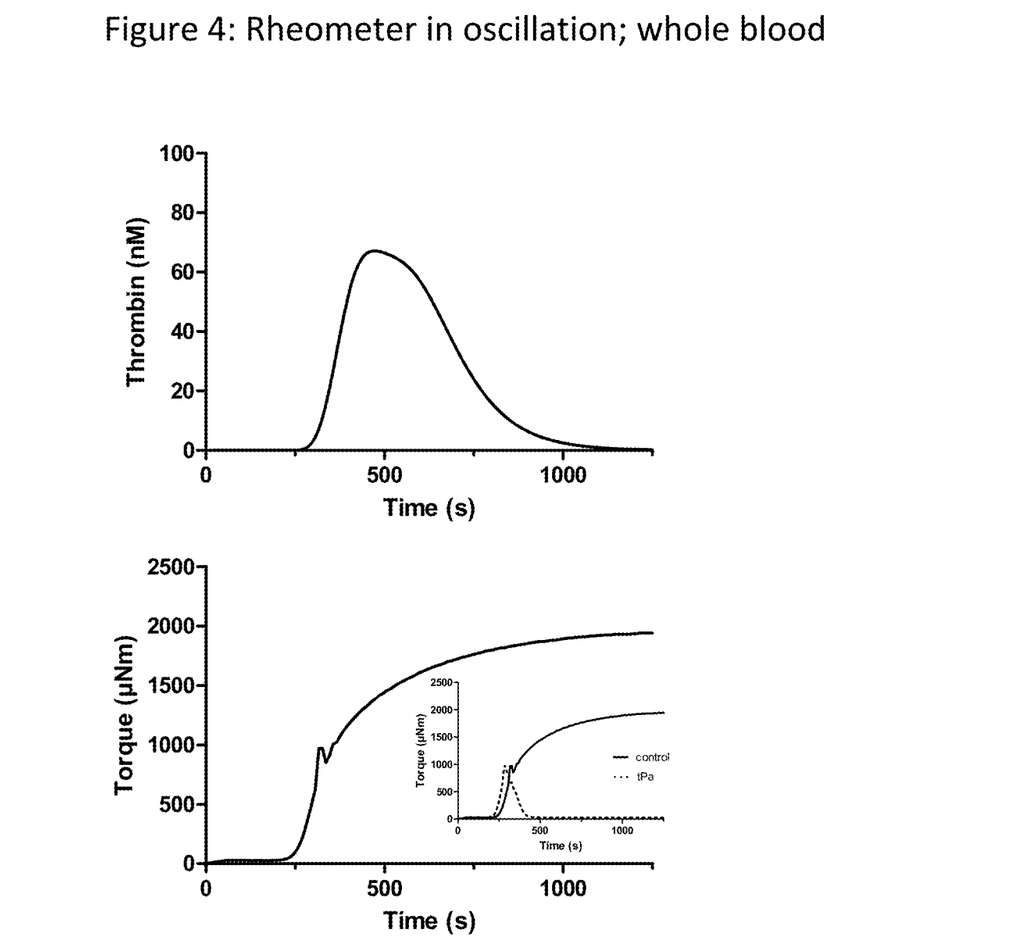
FIG. 4 shows the simultaneously measured thrombin generation curve and viscosity plot obtained in a blood sample by a specially designed rheometer (with integrated fluorometer) in oscillation modus.

A rheometer according to an embodiment of the invention, designed to carry out the measurement of proteolytic enzyme generation and the simultaneous measurement of clot strength is shown in FIGS. 2 and 3. Said rheometer comprises a head part 1 having a motor 2 driving a shaft 3 supporting a cone element 4 at its lower end. The tip 5 of the cone element 4 is oriented downward and is facing an upper plate 6 of a base part 7. The angle θ of the cone 4 is for example between 0,1° and 5°, and is preferably 0,5 °.

The head part 1 also comprises means 8 for measuring the rotational speed of the shaft 3 and/or the torque exerted by the motor 2 to the shaft 3. Optionally, a dark hood 9 is slidably mounted on the shaft 3. In this case, the position of the hood 9 can be adjusted by corresponding means 10. The position of the head part 1 relative to the base part 7 is controlled by means 11, in order to set the gap g (measuring gap) between the tip 5 of the cone 4 and the upper plate 6 of the base part 7, or between the tip 5 of the cone 4 and the bottom surface 14' of a holder 14.

A fluorometer 12 is mounted into the base part 7 for quantifying the fluorescence signal emitted by a sample 13 placed on the upper plate 6. The sample 13 is for example inserted into a cup-like holder 14. Both the holder 14 and the upper plate 6 are transparent, at least partially, to enable the quantification of the fluorescence signal emitted by the sample 13.

During an assay, the sample holder 14 is placed on the upper plate 6 of the base part 7 and the cone 4 is lowered by the means 11, to adjust the gap g. Said gap is for example between 10 µm and 2 mm, preferably not more than 100 µm. The hood 9 is also lowered to cover the sample holder 14 so as to avoid any loss of fluorescence signal.

During the assay, the fluorescent signal emitted by the sample 13 is also measured by the fluorometer 12, through the holder 14 and the upper plate 6, in order to determine changes in Thrombin concentration over time.

According to the invention, when using the rheometer, the rotational force applied to the biological sample is selected to reflect the blood in said vascular setting. Hence, for arterial setting the shear rate is in the range of 800 to 3000 s-1; in a venous setting the rotational force is in the range of 50 to 800 s-1. When an oscillatory force is applied it may be in a range of 0.1 s-1 to 300 s-1.

The method of the invention is performed applying a rotational force to the mixture obtained with the biological sample in step a). By rotating the measuring system, the shear rate of venous and arterial blood flow occurring in vivo can be simulated, enabling to study in vitro blood coagulation/clot lysis under flow, rendering information on platelet function and fibrinolysis under conditions that more closely resemble the in vivo situation.

Accordingly, the invention provides reagents and methods to study hemostasis in a physiological setting to determine coagulation propensity or in a pathological setting, especially to determine or to monitor a clinical condition in a patient, or to perform therapy planning or therapy monitoring. In a particular embodiment, the methods, reagents and kits of the invention are used for the determination of a risk to face thrombosis or bleeding in a patient.

The invention, in providing operating conditions mimicking in vivo blood flow may be used to study various vascular settings, in particular arterial, venous or tumor microcirculation.

According to a particular aspect of the present invention said first subsample of the assayed biological sample further comprises a drug or a pharmaceutical agent to be tested, for its influence on the proteolytic system under study, such as the haemostatic-thrombotic system. Suitable pharmaceutical agents which can be tested in the present method are antithrombotic agents, such as anti-platelet agents and anticoagulating agents, for example heparin, dermatan sulphate, a direct thrombin-inhibitor, for example hirudin, argatroban or melagatran, and a factor Xa inhibitor, for example thick anticoagulant protein.

According to another aspect of the invention, the method is performed in order to monitor the effects of drugs administered to a patient on the haemostatic-thrombotic system. Such drugs include anticoagulant drugs, especially all types of heparins, direct thrombin inhibitors or other antithrombodic agents such as those cited above.

By measuring the fluorescence in the thin layer of biological sample formed between the plate containing the assayed biological sample and the measuring system, the effect of the inner filter effect described above is reduced.

The invention also relates to a method as defined herein when used:
- for detecting or monitoring the effect of determined substances, especially a drug or a pharmaceutical agent on thrombin activity and clot strength in a biological sample, wherein said determined substance(s) is (are) added to the sample to be assayed or is (are) added during thrombin generation or
- for monitoring effects of drugs on a biological sample of a patient under treatment with this drug or
- for screening substances to determine their interacting capacity with thrombin generation or fibrinolysis or coagulation,
- to assess deficiencies in molecules in the haemostatic-thrombotic system or,
- to determine the minimal amount of thrombin necessary to initiate clot initiation.

The invention also relates to a kit for the determination of the course of proteolytic enzyme activity and for the simultaneous determination of the strength of the formed fibrin clot in a biological sample, comprising:
- in a disposable sample holder having a transparent bottom surface, suitable for use on a rotary rheometer, a composition of a signal substrate causing a detectable signal related to the conversion product released upon reaction of said signal substrate with the proteolytic enzyme generated in the triggered sample and a composition for triggering the proteolytic enzyme activity in the sample,
- optionally a calibrator compound compound harbouring a constant stable proteolytic enzyme activity on the signal substrate,
- optionally a suitable buffer solution for addition to the biological sample, such as BSA5 buffer comprising 20 mM HEPES and Bovin Serum Albumin 5 mg/ml, at pH=7.35.

EXAMPLES

The invention will now be further illustrated by the following examples which are not to be construed as limiting the scope of the invention in any respect.

Experimental

Reaction Mixture

Blood was obtained through venipuncture (1 volume trisodium citrate 0.13M to 9 volumes blood). Free flow or minimal suction should be employed, and vacuum containers avoided. Platelet poor plasma (PPP) was obtained by centrifugation of blood twice at 2630 g for 10 min.

Recombinant relipidated tissue factor (rTF) not containing polybrene or $Ca^{++}$ was from Dade Behring (Marburg, Germany). For each experiment, a fresh mixture of Tissue Factor (TF) and phospholipids vesicles (PL) (Avanti, Alabaster, Ala., USA) was prepared, resulting in a final concentration of 5 pM TF and 4 µM PL in Hepes buffer (20 mM, pH 7.35) containing 5 mg/l BSA (Sigma, A-7030). Recombinant tissue plasminogen activator (tPA) was obtained from Boehringer Ingelheim GmbH, Germany as actylase™. Fluorogenic substrate, $(Z-Gly-Gly-Arg)_2Rho110$, was obtained from Diagnostica Stago (Asnieres, France) and used at a concentration of 300 µM. Upon splitting by thrombin, it releases the fluorescent rhodamine (Rho), which is measured by a 470 nm excitation and a 520 emission filter set. The fluorogenic plasmin substrate, H-Ala-Leu-Lys-AMC, was obtained from Diagnostica Stago and used at a final concentration of 200 µM. The by plasmin released fluorescent 7-Amino-4-methylcoumarin (AMC) is measured by a 365 nm excitation and a 430 nm emission filter set. A fresh mixture of fluorogenic substrate and $CaCl_2$ (FluCa) was prepared at 37° C. for each experiment, resulting in a final concentration of 300 µM Rho and 16.7 mM $CaCl_2$ in Hepes Buffer (20 mM, pH 7.35) containing 60 g/l BSA.

The calibrator, α2M-Thrombin complex (α2MT), was prepared in house as previously described [2]. The concentration of α2M-Thrombin is measured by its ability to hydrolyze the chromogenic substrate S2238. This amidolytic activity of the preparation was adjusted to have in the final reaction the same activity as 100 nM human thrombin. After adding bovine antithrombin and heparin (LEO) this material was ready for use as a thrombin calibrator.

Using a signal substrate with a fluorescent leaving group, thrombin generation was measured via a fluorescence detector. The strength of the formed fibrin clot was monitored by an oscillating or rotating measuring system of a specially designed rheometer (Physica MCR 301, Anton Paar Germany GmbH, Ostfildern).

A total of 700 µl (in case of plasma) or 800 µl (in case of blood) sample and substrate was added on the thermostated sample holder at 37° C. of the rheometer. This mixture contained (and was prepared by adding in the following order) sample (468 µl plasma or 700 µl blood); TF-PL mix (or calibrator) (116 µl in case of plasma; 50 µl in case of blood) and FluCa (116 µl in case of plasma; 50 µl in case of blood). Immediately after addition of the FluCa, the viscosity (or Torque in case of oscillation of the measuring system) and fluorescence were measured every 10 seconds and every second at 470/520 nm respectively.

Example 1

Thrombin Generation in Relation to Clot Strength Based on Viscosity Detection

Thrombin generation was triggered in whole blood as indicated above on the glass of an MCR301 rheometer with a built-in fluorometer. Immediately after addition of the FluCa solution, the measuring system of the rheometer was set to a zero gap position and brought into oscillation, at a frequency of 10 Hz and an angle of 1°. Torque and fluorescence were measured as indicated above, both for the triggered sample (first part of the sample, i.e., first subsample) and the sample containing the calibrator (second part of the sample, i.e., second subsample). The use of the calibrator avoids the donor-dependent influence of the fluorescent signal through absorption of light and quenching of the fluorescence. Based on the calibrator curve and after correction for the α2M-thrombin present in the sample which is still able to convert the substrate, the thrombin generation curve for the triggered sample was determined, as described above. The mean of two measurements is shown in FIG. 3 (upper panel). Clot initiation (shown as Torque in the lower panel) already started at the very beginning of the thrombin generation. Interestingly, by adding tissue plasminogen activator (tPA) at a concentration of 300 U/ml, fibrinolysis could be followed in the blood sample (inset).

Example 2

Figure 5A:
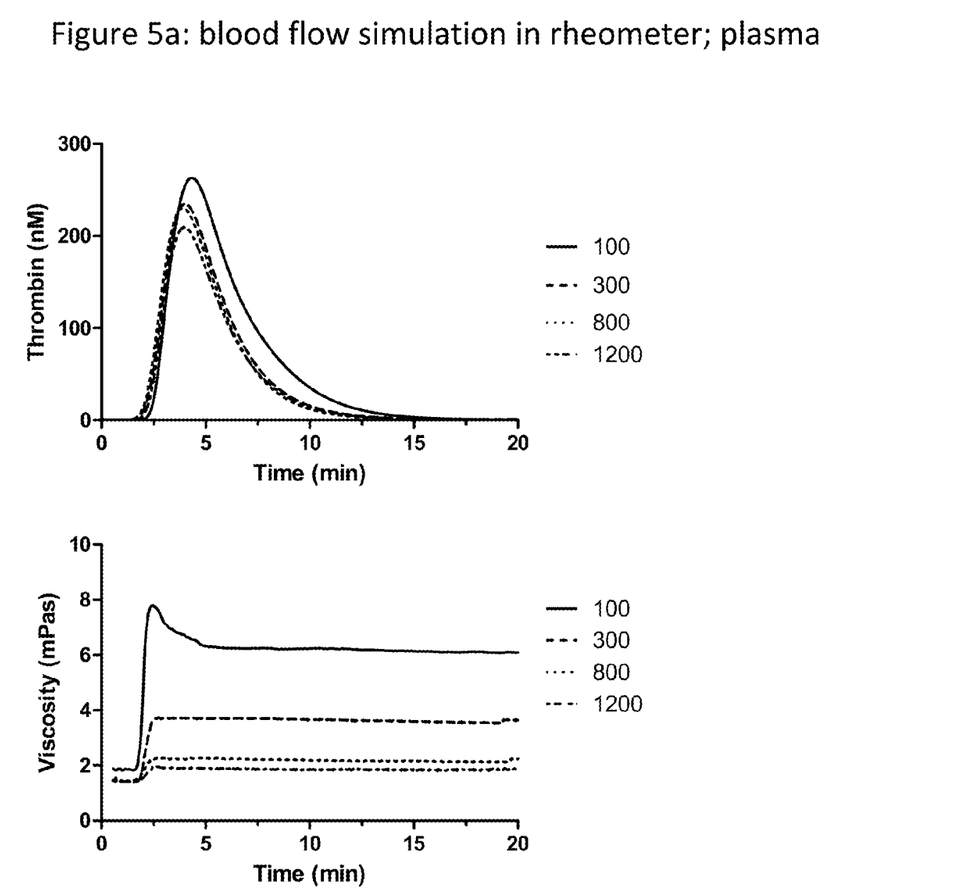
FIG. 5 shows the simultaneously measured thrombin generation curve and viscosity plot obtained in a platelet-poor plasma (a) and whole blood (b) sample by a specially designed rheometer of the invention with integrated fluorometer. Different shear rates were used to simulate venous and arterial flow.
Figure 5B:
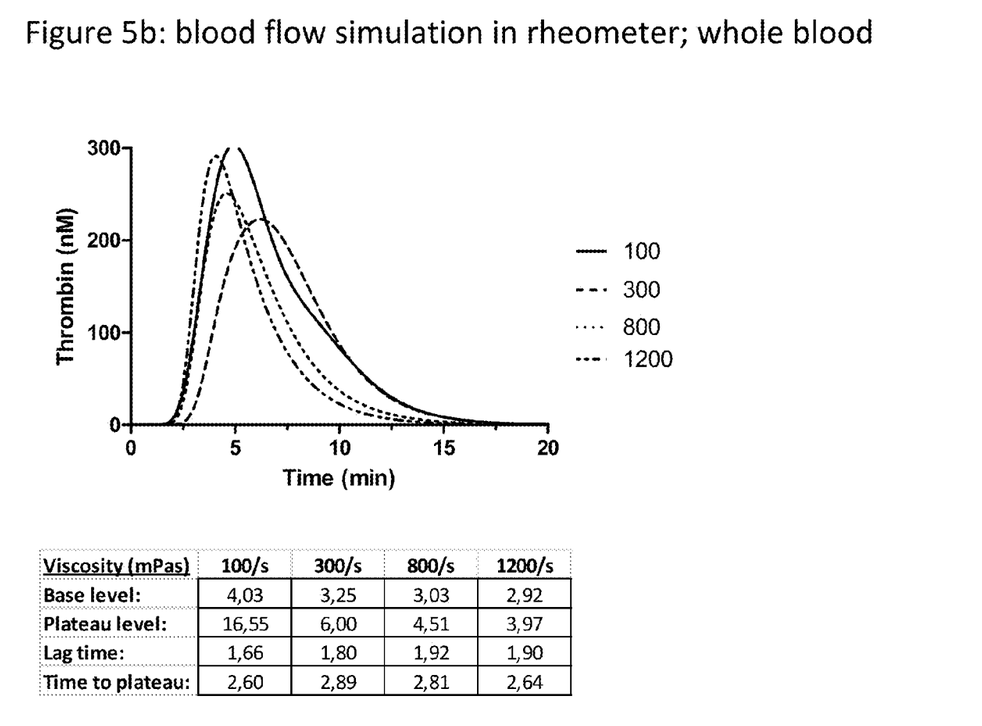

Thrombin Generation in Relation to Fibrin Formation Based on Viscosity Detection; Simulation of Blood Flow Thrombin generation was triggered in platelet-poor plasma or whole blood as indicated above on the glass of an MCR301 rheometer with a built-in fluorometer. Immediately after addition of the FluCa solution, the measuring system of the rheometer was set to a zero gap position and brought into rotation. This rotation of the measuring system allowed simulation of the blood flow, a shear rate of 100-300/s corresponding to venous blood flow and above 800/s to arterial blood flow. Viscosity and fluorescence were measured as indicated above, both for the triggered sample and the sample containing the calibrator. Measurements were done in triplicate and the mean is shown in FIG. 5a (platelet-poor plasma) and 5b (whole blood). In platelet-poor plasma, shear rates higher than 100/s resulted in decreased thrombin generation and clot strength. The effect on clot strength was repeated in whole blood, however the effect on thrombin generation was different.

Example 3

Figure 6:
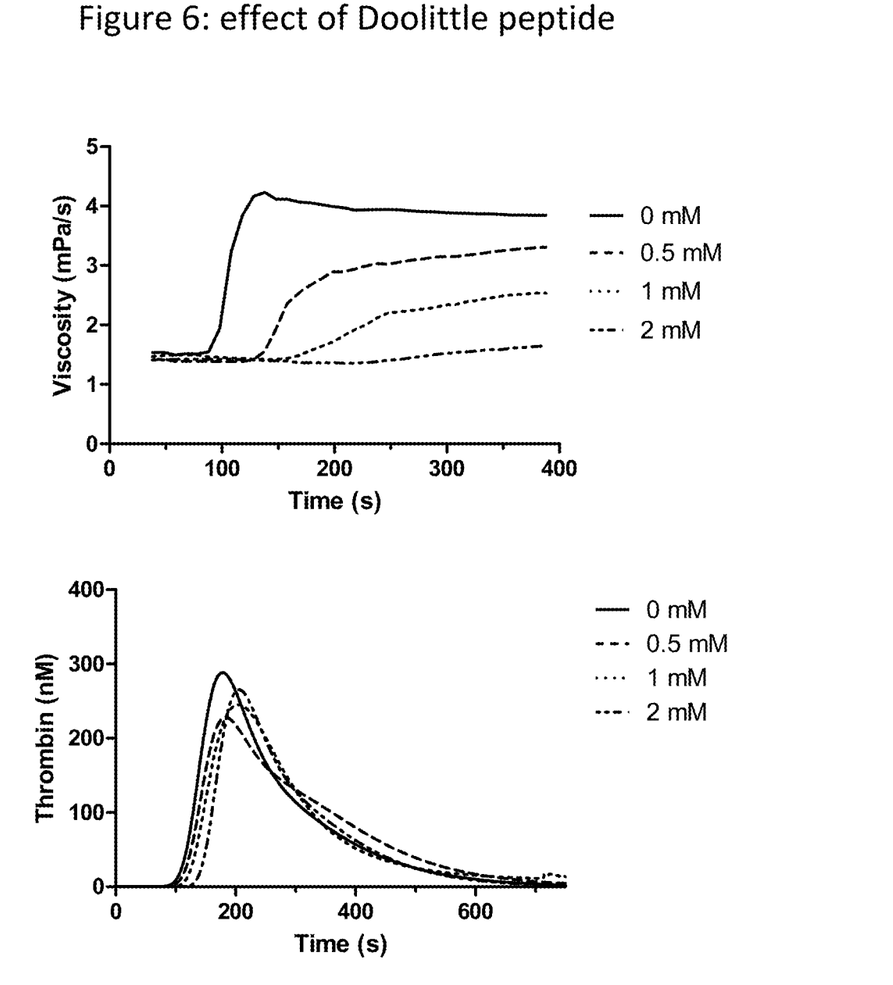
FIG. 6 shows the effect of Doolittle peptide on the viscosity plot and thrombin generation curve in platelet-poor plasma as measured by a specially designed rheometer.

Visualization of the Effect of Doolittle Peptide on Thrombin Generation and Clot Strength Thrombin generation was triggered in platelet-poor plasma as indicated above on the glass of an MCR301 rheometer with a built-in fluorometer. Increasing concentrations of Doolittle peptide (Gly-Pro-Arg-Pro), 0.5 mM up to 2 mM, were added to the sample and corresponding calibrator. Doolittle peptide binds with a high affinity to fibrinogen, resulting in the inhibition of fibrin polymerization. Immediately after addition of the FluCa solution, the measuring system of the rheometer was set to a zero gap position and brought into rotation, resulting in a shear rate of 300/s. Viscosity and fluorescence were measured as indicated above both for the triggered sample and the sample containing the calibrator. Measurements were done in duplicate and the mean is shown in FIG. 6. As expected, increasing amounts of Doolittle peptide significantly decreased the viscosity of the sample compared to the control sample (upper panel). The effect on the thrombin generation was minimal (lower panel).

Example 4

Thrombin Generation and Clot Strength in Control Versus Defibrinylated Plasma

Figure 7:
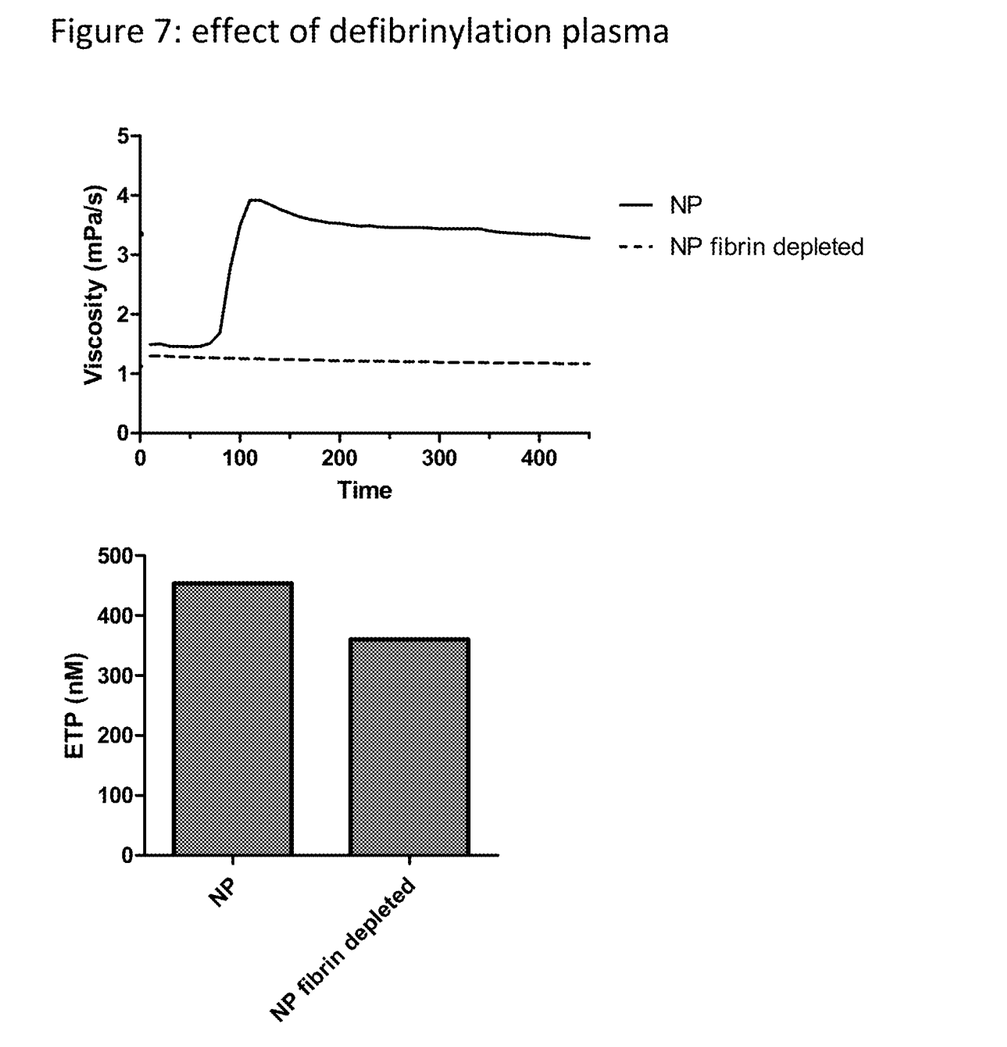
FIG. 7 shows the simultaneously measured thrombin generation results (ETP values) and viscosity plot in defibrinylated versus control platelet-poor plasma by a specially designed rheometer.

Thrombin generation was triggered in control and defibrinylated plasma as indicated above on the glass of an MCR301 rheometer with a built-in fluorometer. Immediately after addition of the FluCa solution, the measuring system of the rheometer was set to a zero gap position and brought into rotation, resulting in a shear rate of 300/s. Viscosity and fluorescence were measured as indicated above. Results are shown in FIG. 7. As expected, defibrinylation of plasma resulted in the complete abolishment of the increase in viscosity (upper panel) without a clear effect on the thrombin generation (depicted as ETP; lower panel).

Example 5

Figure 8:
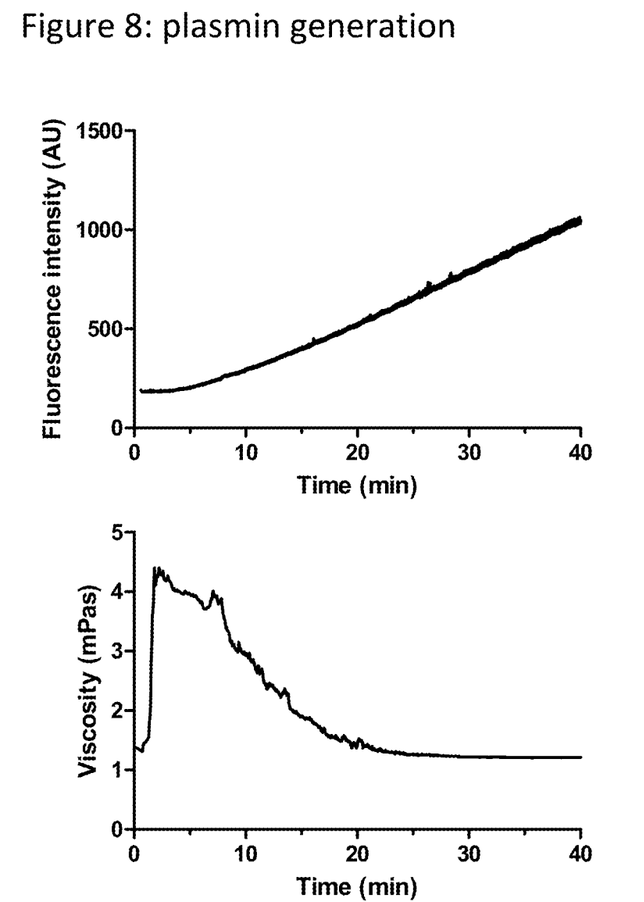
FIG. 8 shows the raw fluorescence data of the plasmin generation in platelet-poor plasma, together with the simultaneously measured viscosity plot.

Plasmin Generation and Clot Strength in Tissue Plasminogen Activator-Triggered Platelet-Poor Plasma Clot initiation was triggered in platelet-poor plasma as indicated above in the presence of 100 U/ml tPA on the glass of an MCR301 rheometer with a built-in fluorometer. Immediately after addition of the plasmin substrate solution containing Ca, the measuring system of the rheometer was set to the measuring gap position and brought into rotation (300/s). Fluorescence and viscosity were measured as indicated above, both for the triggered sample and the sample containing the calibrator. Raw fluorescence and viscosity data are shown in the upper and lower panel of FIG. 8, respectively. Results clearly indicate activation of plasmin by tPA, resulting in the degradation of fibrin (decrease in viscosity).

The present invention accordingly offers a convenient test method to determine simultaneously and in real time the course of a proteolytic activity, in particular thrombin activity, and the strength of the clot in a blood/plasma sample. The test provides a continuous signal thereby giving more valuable and accurate information regarding such parameters as lag time, peak height and time to peak as compared with methods that only use end-point determinations of the amount of product formed. Importantly, the present invention allows the in vitro investigation of thrombin generation and clot strength in conditions resembling in vivo shear rates in venous and arterial blood flow, enabling valuable information on platelet function and fibrinolysis. Simulating shear rates of venous and arterial blood flow is important given the fact that a clot must resist shear stress at the site of the injury.

REFERENCES

1 Konings J, Govers-Riemslag J W, Philippou H, Mutch N J, Borissoff J I, Allan P, Mohan S, Tans G, Ten Cate H, Ariens R A. Factor XIIa regulates the structure of the fibrin clot independently of thrombin generation through direct interaction with fibrin. *Blood.* 2011; 118: 3942-51.
2 Hemker H C, Giesen P, Al Dieri R, Regnault V, de Smedt E, Wagenvoord R, Lecompte T, Beguin S. Calibrated automated thrombin generation measurement in clotting plasma. *Pathophysiol Haemost Thromb.* 2003; 33: 4-15.
3 Beguin S, Kumar R. Thrombin, fibrin and platelets: a resonance loop in which von Willebrand factor is a necessary link. *Thromb Haemost.* 1997; 78: 590-4.
4 Kumar R, Beguin S, Hemker H C. The influence of fibrinogen and fibrin on thrombin generation—evidence for feedback activation of the clotting system by clot bound thrombin. *Thromb Haemost.* 1994; 72: 713-21.
5 Kumar R, Beguin S, Hemker H C. The effect of fibrin clots and clot-bound thrombin on the development of platelet procoagulant activity. *Thromb Haemost.* 1995; 74: 962-8.
6 Biggs R, Macfarlane G. *Human blood coagulation and its disorders.* Oxford: Blackwell Scientific, 1953.

7 Seegers W H. *Prothrombin*. Cambridge, Mass.,: Published for the Commonwealth Fund by Harvard University Press, 1962.
8 Hemker H C, Beguin S. Thrombin generation in plasma: its assessment via the endogenous thrombin potential. *Thromb Haemost*. 1995; 74: 134-8.
9 Hemker H C, Wielders S, Kessels H, Beguin S. Continuous registration of thrombin generation in plasma, its use for the determination of the thrombin potential. *Thromb Haemost*. 1993; 70: 617-24.
10 Hemker H C, Giesen P L, Ramjee M, Wagenvoord R, Beguin S. The thrombogram: monitoring thrombin generation in platelet-rich plasma. *Thromb Haemost*. 2000; 83: 589-91.
11 Bolliger D, Seeberger M D, Tanaka K A. Principles and practice of thromboelastography in clinical coagulation management and transfusion practice. *Transfus Med Rev*. 2012; 26: 1-13.
12 Rivard G E, Brummel-Ziedins K E, Mann K G, Fan L, Hofer A, Cohen E. Evaluation of the profile of thrombin generation during the process of whole blood clotting as assessed by thrombelastography. *J Thromb Haemost*. 2005; 3: 2039-43.
13 Sorensen B, Johansen P, Christiansen K, Woelke M, Ingerslev J. Whole blood coagulation thrombelastographic profiles employing minimal tissue factor activation. *J Thromb Haemost*. 2003; 1: 551-8.

The invention claimed is:

1. A method for simultaneously determining in real time proteolytic enzyme activity and strength of a fibrin clot formed in a biological sample in a single apparatus, the proteolytic enzyme activity being measured through detection of a signal of a conversion product released upon reaction of a signal substrate with the proteolytic enzyme, the strength of the fibrin clot being measured through a rheometer measuring system, while simulating in vivo blood flow conditions, the method comprising the following steps:
    a. triggering proteolytic enzyme generation in the biological sample so as to enable clotting in said biological sample, and contacting said biological sample with a signal substrate causing a detectable signal related to a conversion product released upon reaction of said signal substrate with the proteolytic enzyme generated, thereby providing a sample mixture,
    b. displaying the sample mixture obtained in step a) as a thin layer in a sample holder, and setting a measuring gap between a rheometer measuring system and said sample mixture, the sample holder being suitable for measurement of a detectable signal obtained after reaction of the signal substrate with the proteolytic enzyme,
    c. applying a rotational force to the sample mixture obtained in step b) through the rheometer measuring system, thereby simulating in vivo venous or arterial blood flow of a determined in vivo physiological or clinical condition,
    d. determining the proteolytic enzyme activity by measuring the development of the detectable signal in the sample mixture obtained in step c) over a period of time and
    e. determining simultaneously the strength of the fibrin clot formed in the sample mixture obtained in step c) by measuring the increase in viscosity of the sample mixture obtained in step c) over a period of time with a rheometer measuring system.

2. The method according to claim 1, further comprising an initial step of dividing the biological sample in at least two parts, designated as a first subsample and a second subsample, and wherein steps a) to e) are performed on the first subsample and the following steps f) to i) are performed on the second subsample for calibration of the results of measurement of the activity of the determined proteolytic enzyme:
    f) adding to the second subsample, which is a non-clotting subsample, a calibrator compound maintaining a constant and stable activity on the signal substrate for said determined proteolytic enzyme, said calibrator compound being otherwise inert in the coagulation reactions of the subsample, and contacting the obtained mixture of said calibrator compound and second subsample with a signal substrate causing a detectable signal related to the conversion product released upon reaction of said signal substrate with the proteolytic enzyme of said second subsample,
    g) submitting the mixture obtained in step f) with the second subsample to steps b) and c) defined in claim 1,
    h) determining the proteolytic enzyme activity by measuring the development of detectable signal in the sample mixture obtained in step g) over a period of time,
    i) comparing the proteolytic enzyme activity obtained in step h) for the second subsample to the proteolytic enzyme activity obtained in step d) for the first subsample, and providing calibrated proteolytic enzyme activity over time for the first subsample.

3. The method according to claim 1, wherein an oscillary force is applied on the mixture obtained in step b) in addition to the rotational force.

4. The method according to claim 1, wherein the biological sample is selected from the group consisting of whole blood, platelet-rich plasma, platelet-poor plasma and platelet-free plasma.

5. The method according to claim 1, wherein the proteolytic activity is selected from the group consisting of activated clotting factor activity, activated fibrinolytic factor activity, and activated component of the complement system activity.

6. The method according to claim 1, wherein the proteolytic enzyme activity is thrombin activity.

7. The method according to claim 1, wherein the signal substrate is selected from the group consisting of compounds comprising a leaving group, selectively released as a detectable conversion product upon reaction of the signal substrate with the proteolytic enzyme formed.

8. The method according to claim 7, wherein the proteolytic enzyme formed is thrombin and the signal substrate is a fluorogenic substrate selectively hydrolyzed by thrombin, having a moderate binding affinity for thrombin and a low kinetic constant.

9. The method according to claim 8, wherein the fluorogenic substrate is an oligopeptide having a sequence of 2 to 30 amino acids residues coupled with a fluorescent molecule.

10. The method according to claim 9, wherein the oligopeptide has a terminal lysine or arginine for coupling with a fluorescent molecule.

11. The method according to claim 10, wherein the signal substrate is (Z-Gly-Gly-Arg)$_2$Rho110 or Z-Gly-Gly-Arg-AMC.

12. The method according to claim 1, wherein
    the protease activator triggering the biological sample is selected from the group consisting of phospholipids, tissue factor, soluble tissue factor, thromboplastin, kaolin, and elagic acid, and
    the reagent eliciting coagulation reaction is calcium ion.

13. The method according to claim 2, wherein an oscillary force is applied on the mixture obtained in step b) in addition to the rotational force.

14. The method according to claim 1, wherein step d) further comprises providing a curve of proteolytic enzyme activity over time showing development of the detectable signal in the sample mixture obtained in c) over a period of time.

15. The method according to claim 1, wherein in step b) the measuring gap set between a rheometer measuring system and the sample mixture is a zero gap.

16. The method according to claim 2, wherein step h) further comprises providing a curve of proteolytic enzyme activity over time showing the development of the detectable signal in the sample mixture obtained in g) over a period of time.

17. The method according to claim 2, wherein step i) further comprises providing a calibrated curve for the proteolytic enzyme activity of the first subsample.

\* \* \* \* \*